United States Patent [19]

Manabe et al.

[11] Patent Number: 4,472,505
[45] Date of Patent: Sep. 18, 1984

[54] METHOD OF ANALYZING CHEMICAL SUBSTANCES

[75] Inventors: Sugio Manabe, Kodaira; Taiichi Banno; Nagahiro Gocho, both of Hachioji; Masahiko Sakurada, Machida; Ryoichi Orimo, Ohme, all of Japan

[73] Assignee: Olympus Optical Co. Ltd., Japan

[21] Appl. No.: 258,549

[22] Filed: Apr. 29, 1981

[30] Foreign Application Priority Data

May 2, 1980 [JP] Japan .................... 55-59174

[51] Int. Cl.$^3$ .............. G01N 35/00; G01N 33/48; G01N 21/00
[52] U.S. Cl. .................... 436/47; 364/498; 422/65; 422/67
[58] Field of Search ............ 23/230 R, 230 A; 422/67; 364/497, 498; 436/43, 47

[56] References Cited

U.S. PATENT DOCUMENTS

| | | | |
|---|---|---|---|
| 3,639,738 | 2/1972 | Laukien | 364/498 |
| 3,902,052 | 8/1975 | Amar | 364/497 X |
| 4,140,394 | 2/1979 | Roos | 364/498 X |
| 4,234,538 | 11/1980 | Ginsberg et al. | 422/64 |
| 4,236,894 | 12/1980 | Sommervold | 422/67 X |
| 4,338,279 | 7/1982 | Orimo et al. | 422/67 |

OTHER PUBLICATIONS

Laboratory Medicine, vol. 5, No. 5, May 1974, pp. 34-36.

Primary Examiner—Michael S. Marcus
Attorney, Agent, or Firm—Parkhurst & Oliff

[57] ABSTRACT

A method of enhancing the accuracy and reliability of a chemical analysis, wherein a reaction is carried out by combining a sample liquid with at least one reagent to form a test liquid and the test liquid is photometrically scrutinized a plurality of times over an extended period of time to derive a number of photometric values. The derived values are then stored and a plurality of the stored photometric values are preliminarily selected from a given time frame, wherein the plurality of preliminarily selected values are less than a total number of stored photometric values. Successive preliminarily selected photometric values are compared with at least one predetermined standard to derive a comparison result and upon indication that useful data cannot be calculated from the preliminarily selected photometric values, a secondarily selecting step of selecting at least one photometric value from all of the stored photometric values, which were not preliminarily selected, is used to derive an analytical result which represents a concentration of a chemical substance in the test liquid or an activity of the test liquid.

14 Claims, 8 Drawing Figures

METHOD OF ANALYZING CHEMICAL SUBSTANCES

BACKGROUND OF THE INVENTION

The present invention relates generally to a clinical chemical analyzing technique, and more particularly to an absorptiometric method of measuring concentrations and/or activities of chemical substances in sample liquids, in an accurate manner with a wide measurement range by measuring variations of absorbance with respect to time.

Such a method of measuring the concentrations and activities of substances by detecting variations of absorbance or optical density is sometimes called as kinetic assay and has been used for measuring an initial rate of reaction. In general, a reaction is carried out by combining a sample liquid with a reagent. Proceeding of reaction depends upon respective test items. FIG. 1 shows a typical curve representing a variation of absorbance with respect to time. The reaction process comprises a lag phase (a) in which the reaction proceeds slowly, a linear phase (b) in which the reaction proceeds linearly and an endpoint phase (c) in which the reaction is completed. In order to improve an accuracy of measurement of kinetic assay, it is absolutely necessary to effect measurement in the linear phase (b). For this purpose, various methods have been proposed. For instance, in one of known methods a measurement start point and a measurement end point have been previously determined for respective test items, and a measurement period defined by these points is divided into two halves. Values measured in these two halves are compared with each other to determine whether or not the measurement has been carried out in the linear phase (b). When the measurement is judged to be out of the linear phase (b), any analytical result is not calculated and an abnormal mark is printed out. However, in this known method, when the abnormal mark is printed out for a certain sample, the measurement has to be carried out again for the relevant sample and thus, an analyzing efficiency will be decreased. In order to increase the efficiency to effect accurate measurements in a short time period, it is necessary to increase the number of measurements for respective samples. That is to say, the number of samplings for measuring the absorbance change has to be increased to get a great amount of data and the data has to be processed statistically. Further, an admission of the lineality is judged on the basis of the following inequality.

$$\frac{|A - B|}{\frac{A + B}{2}} \times 100 \geq 10\%$$

wherein A and B are values measured in the front and back half periods, respectively. When the effectiveness of measurements is checked only by such an inequality, an influence of the lag phase could not be removed unless strict conditions would be imparted. If the condition is too strict, the abnormal mark might be printed out unnecessarily, even if variations are quite small.

In a Japanese Patent Application Laid-Open Publication No. 113,383/79 there is described another known absorptiometric method for measuring chemical substances. In this method, absorbances of respective test liquids are measured at three different time points. At first a variation in absorbance between first two measuring points is derived and is then compared with a standard value of variation. When the measured variation is larger than the standard value, i.e. when the sample contains given substance by a sufficiently large amount or when the activity of the sample is sufficiently high, the concentration or the activity of the given substance is calculated from the measured variation of absorbance. On the other hand, when the concentration or activity of the substance to be measured is low, the concentration or activity is calculated from a variation of absorbance derived from the measured absorbance values at the first and third measuring points. In this method since the concentration or activity is simply calculated from a difference between the absorbances measured at the two points in case of the high concentration, an accurate measurement could not be expected. In order to increase the measuring accuracy, it is preferable to gather data measured at several points and to use only data in the linear region, even in case of high concentration. Further, according to the known method the measuring range is only widened in case of low concentration and the reaction is not actually monitored during said range and thus, the reaction process could not be known and a high reliability could not be obtained. Moreover the absorbance measured at the first measuring point is always used. However, in particular, in case of enzyme catalyzed reaction measurement, the lag phase (a) is relatively long and the value measured at the first point is liable to be subjected to the influence of lag phase. Therefore, the measurement could not be carried out accurately.

In known methods, when the amount of a given substance of a sample to be measured is very small, which results in a very small variation in absorbance, the sample is usually treated as "measurement impossible". In this manner the ability of analysis is limited to a great extent. Further, if the absorbance per se or the variation in absorbance is abnormally high, the data is wasted as "abnormal data". Even in such a case it is preferable to derive analytic results as accurate as possible. However, if the analytic result thus obtained is derived as it is, it could not be distinguished from analytic results which are obtained by normal treatment. This is sometimes undesirable.

SUMMARY OF THE INVENTION

The present invention has for its object to provide a novel and useful method of analyzing chemical substances in sample liquids, which can obviate the above mentioned drawbacks of the known methods and can perform a highly accurate and reliable analysis with a high efficiency over a wide measurement range.

According to the invention a method of analyzing chemical substances in sample liquids comprises: a step of carrying out a given reaction by combining a sample liquid with at least one given reagent to form a test liquid; a step of photometering the test liquid at a plurality of timings during a reaction procedure of the test liquid to derive a plurality of photometric values; a step of storing the plurality of photometric values thus derived; a step of selecting, from the plurality of photometric values thus stored, desired photometric values in accordance with predetermined standard for judgement; and a step of deriving an analytic result representing a concentration of the chemical substance in the test liquid or an activity of the test liquid in accordance with the selected photometric values.

DETAILED DESCRIPTION OF THE PREFERRED EMBODIMENTS

Figure 1:
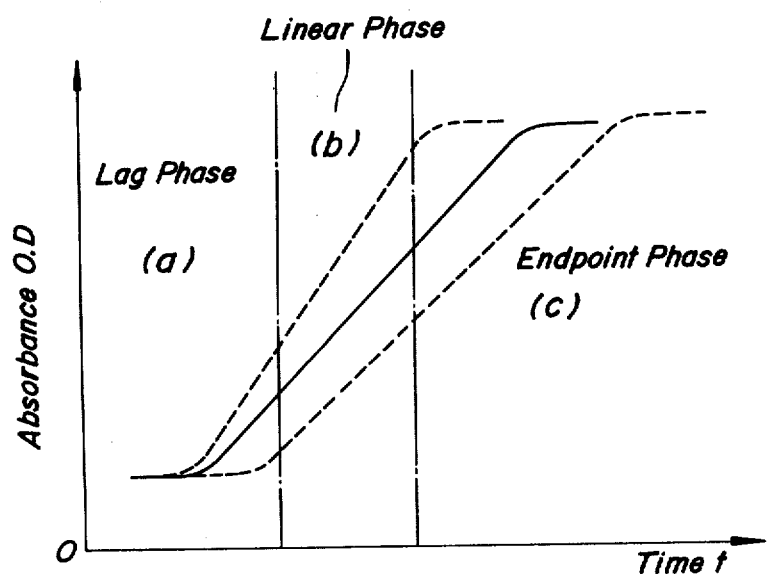
FIG. 1 is a graph showing a typical reaction curve.
Figure 2:
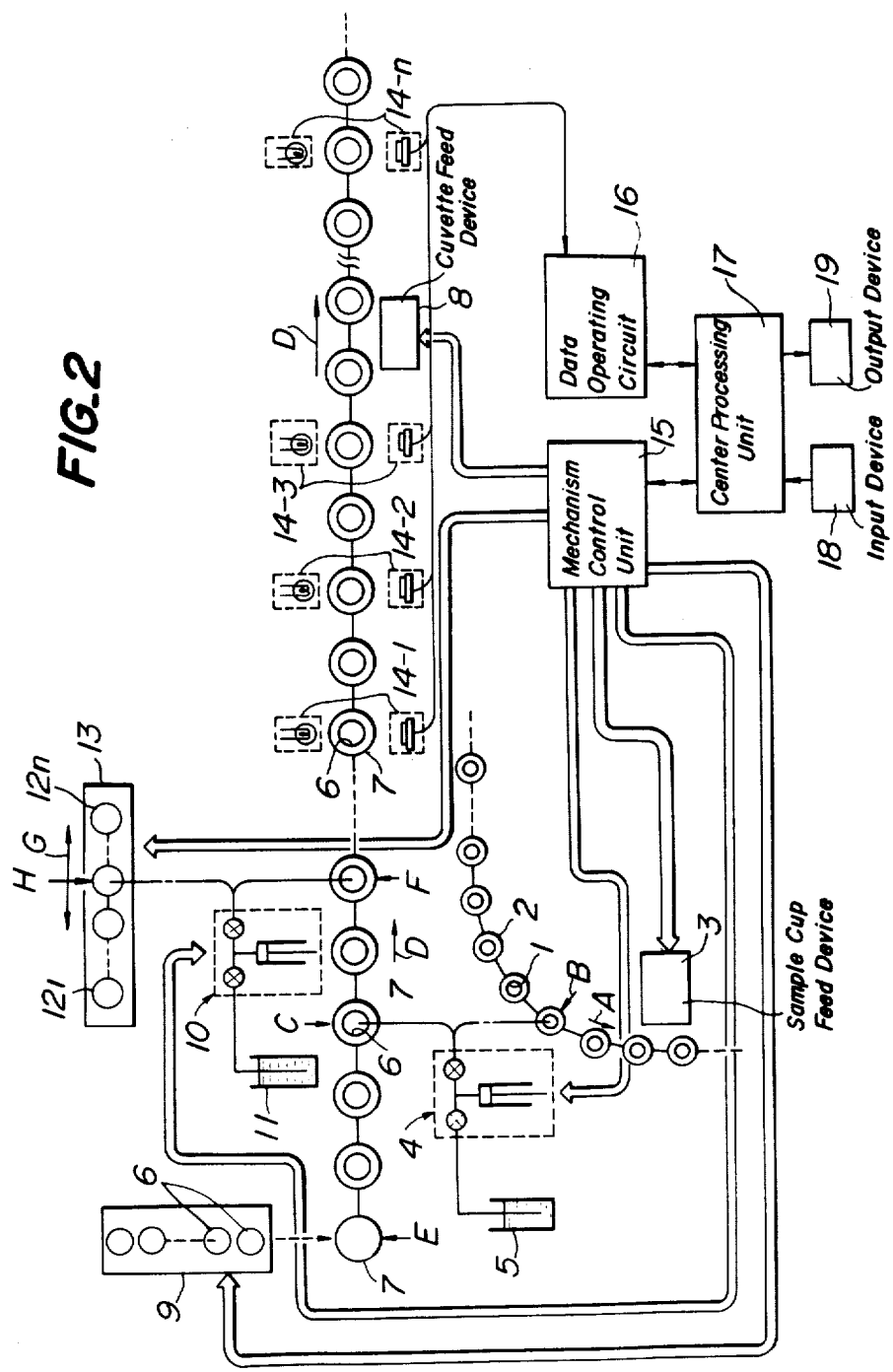
FIG. 2 is a diagram illustrating schematically an embodiment of an automatic chemical analyzer for carrying out the method according to the invention.

FIG. 2 is a schematic view showing diagrammatically a principal construction of an embodiment of an automatic chemical analyzer performing the analyzing method according to the present invention. The automatic chemical analyzer is of a discrete system adopting a batch process and of a sequential-multi system in which a number of test items can be analyzed in succession. A number of sample cups 1 each containing respective sample liquids are held by a sample cup holding unit 2 which may be constructed as a snake chain. The unit 2 is intermittently fed in a direction shown by an arrow A by means of a sample cup holding unit feeding device 3. A sample liquid contained in a sample cup 1 staying at a sample sucking position B is sucked by means of a sample delivery device 4 by a given amount corresponding to one or more test items to be measured for the relevant sample liquid. The sucked sample liquid is delivered into one or more reaction vessels such as cuvettes 6 at a sample delivery position C together with a diluent 5. The cuvettes 6 are held by a cuvette holding unit 7 and are intermittently fed by a feeding device 8 along a reaction line in a direction shown by an arrow D. This intermittent feeding may be effected at a pitch of ten seconds. Into the cuvette holding unit 7 cuvettes 6 are successively supplied at a cuvette supply position E from a cuvette supply device 9. The cuvette 6 into which a given amount of sample liquid has been delivered is advanced by several steps. At a reagent delivery position F, a given amount of a given reagent is supplied into the cuvette 6 by means of a reagent delivery device 10 together with a diluent 11. A plurality of reagents which are required to measure a plurality of test items are contained in respective reagent bottles $12_1$ to $12_n$ which are set in a reagent bottle feed device 13 which is movable in a direction shown by an arrow G. Any desired reagent bottle may be indexed at a reagent sucking position H. In this manner a desired reagent for measuring the given test item can be delivered into the reaction cuvette 6. In the cuvette 6 the sample liquid and reagent can be sufficiently mixed with each other by discharging the reagent and diluent into the cuvette 6 at a suitable velocity by the reagent delivery device 10. Then a given reaction is carried out in the cuvette 6 to form a test liquid. According to the present embodiment the test liquid in the cuvette 6 is measured several times by means of a plurality of photometric colorimeters 14-1 to 14-n, for instance eighteen colorimeters, while the cuvette 6 is fed along the reaction line D. In this manner the reaction condition or reaction procedure can be monitored at a number of measuring points.

The analyzer further comprises a mechanism control unit 15 for controlling the sample cup feed device 3, sample delivery device 4, reaction cuvette feed device 8, reaction cuvette supply device 9, reagent delivery device 10 and reagent bottle feed device 13. The photometric values derived from the photometers 14-1 to 14-n are supplied to a data operating unit 16 and is suitably processed therein. Both the mechanism control unit 15 and the data operating unit 16 are controlled by a center processing unit 17 into which information can be entered from the external by means of an input device 18 and from which information can be displayed or printed by means of an output device 19.

Figure 3:
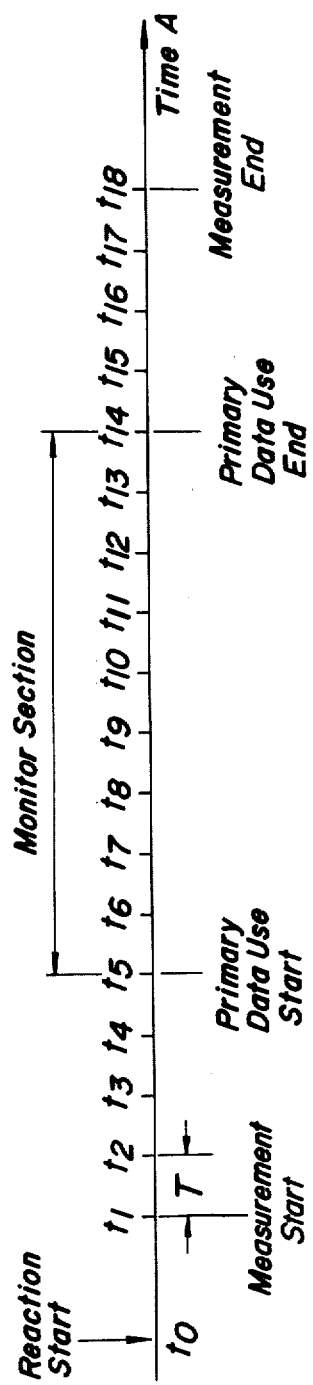
FIG. 3 is a diagram showing a measuring process according to the invention.

FIG. 3 is a timing chart showing various timings of the photometric measurement according to the invention. In this method it is essential that respective test liquids are subjected to a photometry several times. In the embodiment shown in FIG. 2 this is done by a plurality of photometers 14-1 to 14-n arranged along the reaction line D. Alternatively a plurality of photometries may be effected by a single photometer with the test liquid being passed several times through the photometer or with the test liquid being always stayed at the photometer or by a combination thereof. Since the photometry itself is not so important for the present invention, a detailed explanation thereof is not deemed necessary. In the following explanation a plurality of photometries are carried out by a plurality of photometers 14-1 to 14-n as illustrated in FIG. 2.

In FIG. 3 "$t_0$" is a reaction start timing at which a given amount of sample liquid is mixed with a given amount of a given reagent to form a test liquid. "$t_1$" is a first timing at which the test liquid arrives at the first photometer 14-1 and a first measurement is effected thereby. Then the test liquid is measured by successive photometers 14-2 to 14-18. A time period T of the successive measurements is assumed to be twenty seconds. It should be noted that the number of photometers and the time period T of twenty seconds are only exemplary values and any desired values may be selected. According to the invention the test liquid is measured at all photometer positions to derive a plurality of photometric data which are stored in a memory of the center processing unit 17. After that, the photometric data measured in a predetermined section (which will be called as a monitor section hereinafter) is selectively read out and it is judged whether the selected data is useful or not in accordance with a predetermined standard for judgement. In this example, the photometric values obtained by ten photometers 14-5 to 14-14 at timings $t_5$ to $t_{14}$, respectively are preliminarily selected. The standard for judgement will be explained later in detail. When it is determined that the monitor section includes sufficient data for carrying out the analysis accurately and precisely these photometric values are selected to derive analytic results. Therefore, in this case photometric values before a primary data use start timing $t_5$, i.e. the data obtained at timings $t_0$ to $t_4$ and photometric values after a primary data use end timing $t_{14}$, i.e., the data obtained at timings $t_{15}$ to $t_{18}$ are not preliminarily used, even though these values have been stored.

Contrary to this, when the monitor section does not include any useful photometric data, the stored photometric values other than in the monitor section are used to effect the analysis. For instance, in case of analyzing test items such as LDH (lactate dehydrogenase), α-HBD (α-keto butyric dehydrogenase) and ALP (alkaline phosphatase), the reaction proceeds rapidly from the reaction start point $t_0$, it is necessary to use the photometric values obtained at timings $t_0$ to $t_4$. On the contrary, when a change in absorbance is small, it is preferable to measure a variation over a relatively long time. Then it is required to use the photometric values obtained at the later timings $t_{15}$ to $t_{18}$ in order to increase a precision of analysis.

Figure 4:
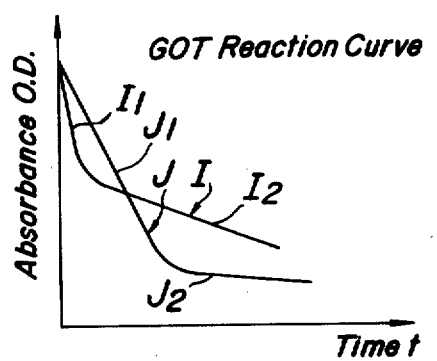
FIG. 4 is a graph depicting a GOT reaction curve.

Next a reason for setting the primary data use point $t_5$ with being delayed with respect to the measurement start point $t_1$ will be explained in detail with reference to FIGS. 4 and 5. FIG. 4 shows a reaction curves I and J of GOT reaction. The curve I consists of a first part $I_1$ in which a reaction due to intrinsic substance is added to a reaction due to substance to be measured at an initial time of reaction, and a second part $I_2$ which is to be measured. The curve J represents a sample of abnormally high activity and consists of a first portion $J_1$ to be measured and a second portion $J_2$ in which substrate is lacking. However, it is impossible to select automatically the second portion $I_2$ for the curve I and the first portion $J_1$ for the curve J. Moreover, it is not absolutely admitted that erroneous results might be produced. Under these circumstances, it is preferable not to use the photometric data obtained in unstable periods.

Figure 5:
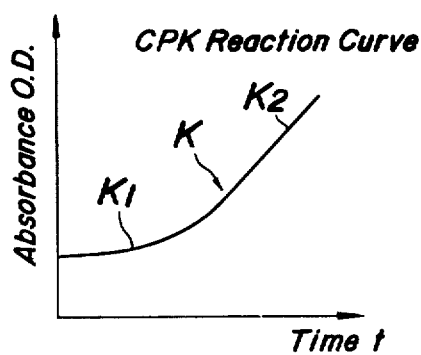
FIG. 5 is a graph showing a CPK reaction curve.

FIG. 5 illustrates a typical reaction curve K for CPK measurement. The curve K consist of a first portion $K_1$ representing the lag phase and a second portion $K_2$ to be measured. The first and second portions $K_1$ and $K_2$ are considered to be linear, but the portion $K_1$ is inherent to the measurement and is not apparently useful. In order to remove such useless data, the primary data use start point $t_5$ is determined after the measurement start point $t_1$ and the photometric values from this point $t_5$ to the primary data use end point $t_{14}$ are preliminarily selected as those in the monitor section. At first a primary judgement is effected with using these values in the monitor section. In this manner the judging operation can be materially simplified as compared with a case in which the whole photometric values are used for judgement.

Figure 6:
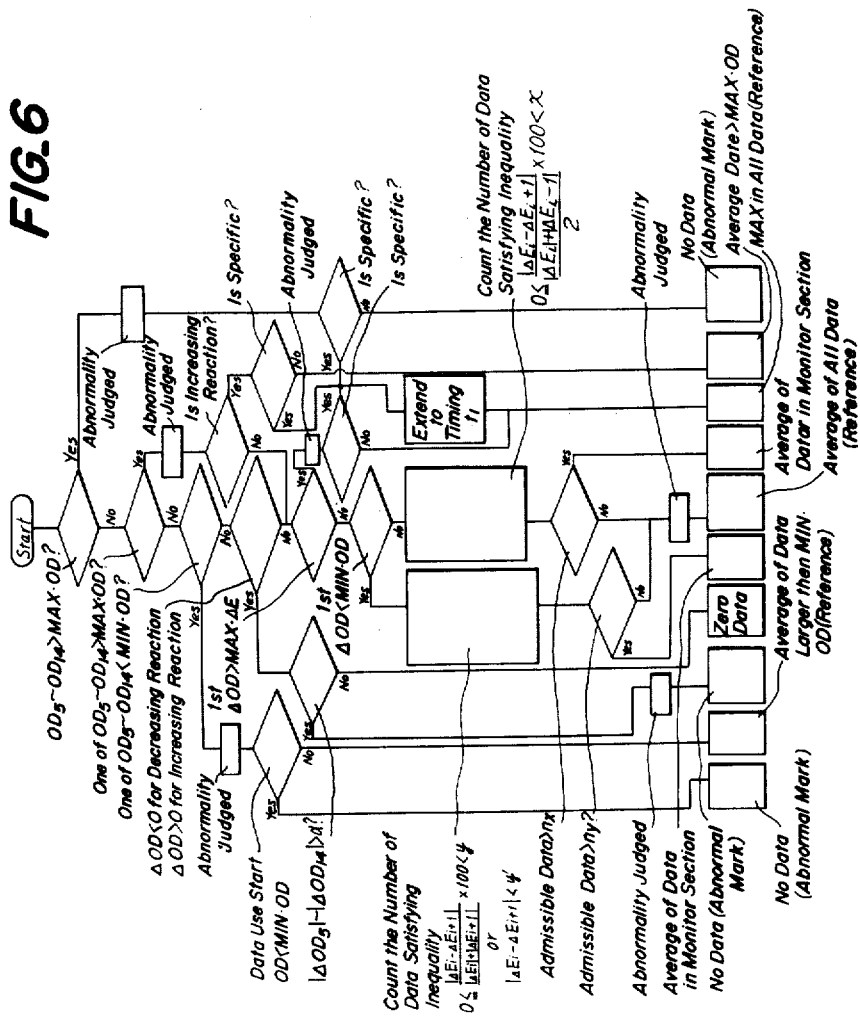
FIG. 6 is a flow chart illustrating a judging step according to the invention.
Figure 7:
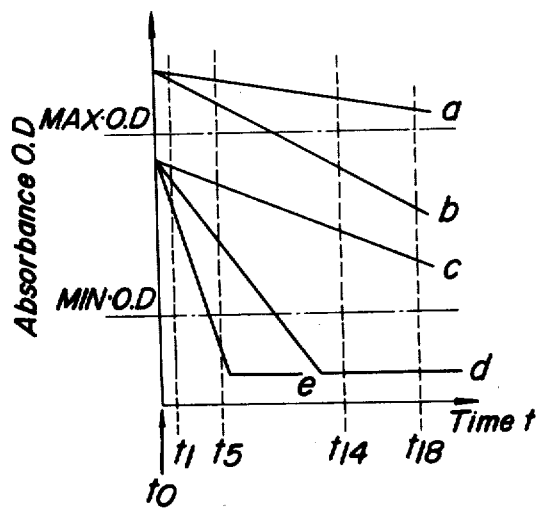
FIGS. 7 and 8 are graphs showing several reaction curves for explaining the method according to the invention.
Figure 8:
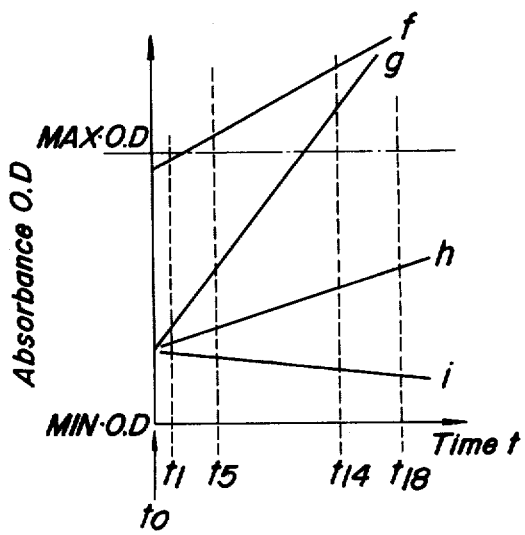

Now the judging standard will be explained in greater detail with reference to FIGS. 6, 7 and 8. FIG. 6 is a flow chart of the judging operation, and FIGS. 7 and 8 show several reaction curves of an absorbance reducing reaction and an absorbance increasing reaction, respectively.

Reaction Curve a

As explained above, according to the invention, a plurality of photometries are effected at eighteen timings $t_1$ to $t_{18}$ to derive eighteen photometric values, i.e. absorbance values, these values are temporarily stored in the memory and ten photometric values within the monitor section are preliminarily selected as primary data. At first it is determined whether or not all of these primary values $OD_5$ to $OD_{14}$ are larger than the maximum absorbance value MAX.OD. As the maximum value MAX.OD an absorbance value of two (OD=2) may be set. In case of the curve a, all of the absorbance values within the monitor section are larger than the MAX.OD=2 and thus, these values are recognized to be abnormal. Then a concentration or activity is no longer calculated. Next it is judged whether or not the relevant test item is specific. When the test item is not specific, no data is derived and an abnormal mark is printed out.

Reaction Curve b

In this case, the absorbance changes within the monitor section in such a manner that at first it exceeds the maximum absorbance value MAX.OD but decreases below the MAX.OD. Then, it is determined whether or not at least one of the ten preliminarily selected photometric values $OD_5$ to $OD_{14}$ within the monitor section exceeds the MAX.OD. In case of the reaction curve b about a half of the photometric values exceed the MAX.OD and this sample is recognized to be abnormal. Next, it is judged whether or not the relevant test item is of the absorbance increasing reaction. Since the test item of the curve b is of the absorbance reducing reaction, then it is further judged whether or not a first absorbance difference ΔOD is larger than the maximum absorbance difference MAX.ΔE. This first absorbance difference ΔOD is a difference between an absorbance value measured at a first timing after the absorbance decreases below the MAX.OD and an absorbance value measured at the next timing. The maximum absorbance difference MAX.ΔE may be suitably determined for respective test items and may be about OD=0.1. When it is judged that the first absorbance difference ΔOD exceeds the MAX.ΔE, an abnormality judgement is once again effected. Then it is further determined whether the relevant test item is specific or not. In this case the test item is not specific. Then among the ten primary absorbance values $OD_5$ to $OD_{14}$, are selected those values which are smaller than the maximum absorbance MAX.OD and the maximum absorbance change among absorbance changes calculated from these selected values is generated as analytic result. In this case it should be noted that since the relevant sample has been once judged as an abnormal one, it cannot be always judged that the derived result is absolutely correct. Therefore the result is printed out together with a special mark such as a star mark indicating that the relevant result is derived for reference. However, according to the invention since the result is obtained by selectively using the data as accurate as possible, the derived result has a relatively high reliability even if the result is for reference.

Contrary to the above, when the first absorbance difference ΔOD is judged to be smaller than the maximum absorbance change MAX.ΔE, then it is determined whether or not the first absorbance difference ΔOD is smaller than the minimum absorbance change MIN.ΔE. The MIN.ΔE is also suitably predetermined depending upon test items and may be set to, for example, 0.02. When the ΔOD is judged to be larger than the MIN.ΔE, among the ten primary values within the monitor section, are selected those values which can be recognized as correct data in the linear phase. This judgement can be carried out in various ways. In a preferred example of such a judgement, the following inequality may be used.

$$0 \leq \frac{|\Delta Ei - \Delta Ei + 1|}{\frac{|\Delta Ei| + |\Delta Ei + 1|}{2}} \times 100 < x$$

In this inequality, ΔEi is a value of an ith absorbance change, ΔEi+1 is a value of an (i+1)th absorbance change, and the threshold value x may be, for example, set to about 10 to 15 percentages. Then it is judged whether or not the number of data selected in accordance with the last mentioned judgement is larger than a predetermined number $n_x$. This number $n_x$ may be set to 3 to 5. When the number of admissible data is larger than the standard number $n_x$, concentration or activity values are calculated as differences in absorbance values contained in the admissible data which has been selected to be within the linear reaction and then an average of the calculated values is derived as an analytic result. As explained above, this result is obtained by means of the several judgements and thus, its accuracy is quite high. In the last mentioned judgement when the number of admissible data is smaller than the standard number $n_x$, an abnormality is judged and a concentration or activity value is calculated from all the data within the monitor section and this value is derived for reference.

Next a case will be explained in which the first absorbance difference $\Delta OD$ is smaller than the minimum absorbance difference $MIN.\Delta E$. In this case the absorbance values from the measurement start point $t_1$ to the measurement end point $t_{18}$ are all once adopted. Then the data from a measuring point, after which the absorbance value decreases below the maximum absorbance value $MAX.OD$, to the measurement end point $t_{18}$ is preliminarily selected. Then absorbance values which are considered to be admissible as those in the linear reaction are selected in accordance with a given standard for judgement. This standard may be expressed by the following inequality.

$$0 \leq \frac{|\Delta Ei - \Delta Ei + 1|}{\frac{|\Delta Ei| + |\Delta Ei + 1|}{2}} \times 100 < y$$

or $$|\Delta Ei - \Delta Ei + 1| < y'$$

wherein, the value y may be set to about 10 to 15 percentages like as the value x and the value y' may be determined to be about 0.002. When either one of the two inequalities is satisfied, the data is recognized to be admissible.

Next the number of the selected absorbance values which have been judged to be admissible as in the linear reaction is compared with a given standard number $n_y$ which may be set to about 3 to 5 just as in the case of the standard number $n_x$. When it is judged that the number of the selected data is larger than $n_y$, concentration or activity values are calculated from the selected data and then an average of the calculated values is derived as an analytic result. On the contrary, when it is determined that the number of the selected data is not larger than $n_y$, an abnormality is judged and an average concentration or activity value calculated from all the measured data is derived for reference.

Reaction Curve c

In this case the measured absorbance values within the monitor section are smaller than the maximum absorbance $MAX.OD$ and are larger than the minimum absorbance $MIN.OD$. Then it is judged whether or not differences $\Delta OD$ in the absorbance values within the monitor section are positive for the decreasing reaction or negative for the increasing reaction. In this example, the reaction is the decreasing one and the absorbance difference $\Delta OD$ is positive. Therefore the judgement is done as "No". After that the treatment like as for the reaction curve b will be effected.

Reaction Curve d

In case of the reaction curve d, the absorbance value becomes smaller than the minimum absorbance value $MIN.OD$ in the monitor section. Therefore, the data within the monitor section includes the absorbance values smaller than $MIN.OD$, the abnormality is judged preliminarily. Then it is further determined whether or not the absorbance value at the primary data use start point $t_5$ is smaller than the minimum absorbance $MIN.OD$. In this case, "No" is judged. Then the data from the primary data use start point $t_5$ to a timing at which the absorbance becomes smaller than $MIN.OD$ is selected. That is to say all the absorbance values which are larger than $MIN.OD$ are selected from the data within the monitor section. Then concentration or activity values are calculated from the selected values and an average of the calculated values is derived as an analytic result together with the reference mark.

Reaction Curve e

In this case all the absorbance values within the monitor section are smaller than the minimum absorbance value $MIN.OD$. Therefore, just as in the case of the reaction curve d, the abnormality is temporarily judged. Further the absorbance value at the primary data use start point $t_5$ is smaller than $MIN.OD$, a concentration or activity value is no more calculated and an abnormal mark is only printed out.

Reaction Curve f

Since all the measured absorbance values within the monitor section are larger than the maximum absorbance value $MAX.OD$, the abnormality is first judged for the reaction curve f. However, if this test item is a specific one, the data from the start point $t_1$ to the point $t_4$ situating immediately before the primary data use start point $t_5$ is additionally adopted. Then concentration or activity values are calculated from all the data from the measurement start point $t_1$ to the primary data use end point $t_{14}$ and the maximum value among the calculated values is derived for reference. That is to say the data giving the maximum absorbance difference $\Delta OD$ is selected and the output calculated from the selected data is derived as an analytic result for reference.

Reaction Curve g

In this case the absorbance value exceeds the maximum absorbance value $MAX.OD$ within the monitor section. Then the judgement whether or not the data in the monitor section includes the absorbance value larger than $MAX.OD$ is effected as "Yes" and an abnormality is determined. Next it is determined whether or not the relevant reaction is of the increasing one. In the example shown in FIG. 8 the reaction is the increasing one and thus "Yes" judgement is done. Further it is judged whether or not the relevant test item is specific. If the test item is a specific one, the judgement of "Yes" is effected. After that the data use start point is extended from the timing $T_5$ to the measurement start point $t_1$ like as the reaction curve f, and then the data giving the maximum absorbance difference is selected and a concentration or activity value calculated from the selected data is derived as an analytic result for reference.

Reaction Curve h

In case of the reaction curve h, all the absorbance values within the monitor section are smaller than the maximum absorbance MAX.OD and are larger than the minimum absorbance MIN.OD, and the reaction is the increasing one. Therefore, when the judgement whether or not the absorbance differences ΔOD within the monitor section is positive is effected, "No" judgement is derived, because the absorbance differences are negative. Then it is judged whether or not the first absorbance difference ΔOD within the monitor section is larger than the MAX.ΔE. As the result of this judgement, when "Yes" is derived, an abnormality is preliminarily given. Further it is determined whether the relevant test item is specific or not. In this example, "Yes" judgement is effect. After that the range of data to be adopted is widened as explained above with reference to the reaction curve f. Among the data the absorbance values which give the maximum absorbance difference are selected and a concentration or activity value is calculated from the selected absorbance values. This value is printed out together with the reference mark.

Contrary to the above when the first absorbance difference ΔOD is smaller than MAX.ΔE, the data will be treated in the same manner as that explained in connection with the reaction curve b.

Reaction Curve i

In this case, all the absorbance values within the monitor section are smaller than MAX.OD and larger than MIN.OD just as in the case of the reaction curve h. Then it is judged whether or not the absorbance differences within the monitor section is positive. In this case, "Yes" judgement is given. Then it is checked whether or not an absolute value of an absorbance difference between the primary data use start and end points $t_5$ and $t_{14}$ is larger than a predetermined value α. The value α may be set to a relatively small value such as 0.001 to 0.002. When a result of this judgement is "Yes", the abnormality is determined. Then no more calculation is effected and only the abnormal mark is printed out. Contrary to this when it is determined that the above mentioned absolute value of the absorbance difference |ΔOD| is smaller than α, a concentration or activity value of zero (which should be differentiated from no data) is derived as an analytic result. In this manner according to the invention the useful analytic result representing the concentration or activity value of zero can be obtained for such a special sample. In known methods such a sample is treated merely as the abnormal one, because the signal could not be clearly distinguished from noise.

In a preferred embodiment according to the invention, in the case of judging whether the data can be admissible as in the linear reaction range or not, the threshold value is changed in accordance with a concentration of activity value. Further two judging conditions are provided and when either one of them is satisfied, the data is recognized as that in the linear reaction range. The first judging condition is given by the following inequality.

$$0 \leq \frac{|\Delta Ei - \Delta Ei + 1|}{\frac{|\Delta Ei| + |\Delta Ei + 1|}{2}} \times 100 < y$$

wherein ΔEi is an absorbance difference between adjacent measuring points and ΔEi+1 is an absorbance difference between next adjacent measuring points, and y is the threshold value. The second condition is given by the inequality of $$|\Delta Ei - \Delta Ei + 1| < y'$$

wherein y' is the threshold value. In should be noted that a divisor of $$\frac{|\Delta Ei| + |\Delta Ei + 1|}{2}$$

in the first inequality may be replaced by ΔEi.

In a low concentration or activity region, the divisor in the first inequality becomes small and thus, even if a dividend |Ei−ΔEi+1| is small, a whole value is liable to become large. Therefore, the data which is admissible as in the linear reaction region could hardly be obtained. In order to avoid such a drawback, if the threshold value y is determined to be relatively high, in a high concentration or activity region, almost all data will be judged to be admissible as being in the linear reaction region. This is very inconvenient. Therefore, when the threshold value y is changed between the low and high concentration or activity regions, it is possible to effect a very accurate judgement for both the low and high concentration regions. However, when ΔEi is extremely small and is near zero, the threshold value is sometimes exceeded and unnecessarily large amount of data is determined to be abnormal. Then, the second condition is provided and, even if the first condition is not satisfied, it is preferable to judge the data as in the linear reaction region in case of the second condition being satisfied.

The present invention is not limited to the embodiments explained above, but many modifications may be conceived within the scope of the invention.

What is claimed is:

1. A method of analyzing chemical substances in sample liquids comprising the steps of:

carrying out a given reaction by combining a sample liquid with at least one given reagent to form a test liquid;

photometering the test liquid at a plurality of timings during a reaction procedure of the test liquid to derive a plurality of photometric values;

storing the plurality of photometric values thus derived;

preliminary selecting, from the plurality of photometric values thus stored, a plurality of photometric values which are obtained at times within a predetermined time period, the plurality of preliminarily selected values numbering less than the total number of photometric values derived;

comparing the differences between successive preliminarily selected photometric values with at least one predetermined standard for judgement to derive a comparison result;

secondarily selecting at least one photometric value from all the stored photometric values which have not been preliminarily selected, because a result of the comparing step indicated that useful data could not be calculated from the preliminarily selected photometric values; and deriving an analytical result representing a concentration of the chemical substance in the test liquid or an activity of the test liquid in accordance with the secondarily selected at least one photometric value.

2. A method of analyzing chemical substances in sample liquids comprising the sequential steps of:
combining the sample liquid with at least one reagent to cause a reaction and form a test liquid;
photometering the test liquid at a first predetermined plurality of time increments within a primary predetermined time period during the reaction procedure of the test liquid to derive a plurality of photometric values;
storing the plurality of photometric values within the memory of a central processing unit;
determining a secondary time period encompassing at least a majority of the first predetermined time increments and beginning of said primary time period and ending a third plurality of time increments before the end of said primary predetermined time period and simultaneously preliminarily selecting the photometric values derived during said secondary predetermined time period as primary data;
comparing the differences between said successive preliminary selected photometric values utilizing at least one predetermined standard for judgement to determine whether said preliminarily selected photometric values include acceptable photometric values for determining the final analytical result;
secondarily selecting at least one of the photometric values derived within the primary time period but outside of the secondary time period because useful analytic results could not be derived from the preliminarily selected photometric values; and
deriving an analytical result representing a concentration of the chemical substances in the test liquid or an activity in the test liquid based on secondarily selected photometric values.

3. A method according to claim 1, wherein said comparing step utilizing at least one predetermined standard for judgement comprises a step of determining whether each of the activities derived from the respective preliminarily selected photometric values exceeds a threshold value near an extreme value of a linear phase of a calibration curve, and said secondarily selecting step comprises a step of selecting at least one photometric value which gives the activities smaller than said threshold value.

4. A method according to claim 1, wherein said comparing step utilizing at least one predetermined standard for judgement comprises a step of judging whether each of the preliminarily selected photometric values is admissible as being in a linear reaction region, and said secondarily selecting step comprises a step of selecting at least one photometric value which is judged to be admissible data in the linear reaction region.

5. A method according to claim 4, wherein said comparing step utilizing at least one predetermined standard for judgement further comprises a step of judging whether the number of the photometric values which have been judged to be admissible is larger than a predetermined number, and said secondarily selecting step comprises a step of supplying all the preliminarily selected photometric values to the deriving step only when the number of the admissible photometric values is larger than said predetermined number.

6. A method according to claim 1 or 2, wherein said comparing step utilizing at least one predetermined standard for judgement comprises a step of judging whether each of the preliminarily selected photometric values is in a range between predetermined maximum and minimum photometric values, and said secondarily selecting step comprises a step of selecting at least one photometric value which is within said range.

7. A method according to claim 1 or 2, wherein said comparing step utilizing at least one predetermined standard for judgement comprises a step of determining whether each of the activities calculated from the preliminarily selected photometric values is within threshold values near upper and lower limits, respectively, of a normal range of activity, and said secondarily selecting step comprises a step of selecting at least one photometric value which is within said threshold values.

8. A method according to claim 1, wherein said comparing step utilizing at least one predetermined standard for judgement comprises a step of determining whether each of a plurality of absorbance values derived from the preliminarily selected photometric values decreases and increases in accordance with a progress of the given reaction, depending upon the fact that a relevant reaction is of a decreasing reaction and of an increasing reaction, respectively, a step of calculating an absorbance change from the photometric values, when the photometric values do not satisfy the condition, and a step of comparing the calculated absorbance change with a predetermined very small value and said deriving step comprises a step of determining an activity of the relevant reaction to be zero, when the calculated absorbance change is smaller than the predetermined very small value.

9. A method according to claim 8, wherein said predetermined very small value is within a range of 0.001 to 0.002.

10. A method according to claim 1, wherein said comparing step comprises a step for judging whether each of the preliminarily selected photometric values satisfies a predetermined condition, and said secondarily selecting step comprises a step of selecting at least one of the photometric values measured at timings inside and outside said predetermined time period, when any one of the preliminarily selected photometric values does not satisfy said predetermined condition.

11. A method according to claim 10, wherein the selecting of at least one of the photometric values comprises a step of selecting at least one of the preliminarily selected photometric values and at least one of the photometric values outside said predetermined time period.

12. A method according to claim 11, wherein said selecting of at least one of the photometric values comprises a step of selecting all the stored photometric values.

13. A method according to claim 10, wherein said selecting of at least one of the photometric values comprises a step of selecting at least one of the photometric values outside said predetermined time period.

14. A method according to claim 10, 11, 12 or 13, further comprising a step of adding to said analytical result a special mark which represents that the derived analytical result is for reference.

* * * * *